United States Patent [19]
Anderson

[11] 4,262,711
[45] Apr. 21, 1981

[54] MICROPLATE FILLER

[76] Inventor: Joseph A. Anderson, 3350 Stuart St., Denver, Colo. 80212

[21] Appl. No.: 11,877

[22] Filed: Feb. 13, 1979

[51] Int. Cl.³ .............................................. B65B 3/04
[52] U.S. Cl. ................................ 141/238; 141/311 R; 141/329; 222/64
[58] Field of Search ..................... 215/247; 222/80, 82, 222/64, 70, 76, 373, 394, 400.7; 128/214 F; 422/63, 75; 23/230 R; 141/94, 95, 329, 330, 19, 237, 238, 1, 279, 236; 285/137 R; 251/4-10

[56] References Cited

U.S. PATENT DOCUMENTS

| | | | |
|---|---|---|---|
| 3,014,481 | 12/1961 | Rumble, Jr. et al. | 222/64 X |
| 4,058,146 | 11/1977 | Citrin | 141/238 |
| 4,085,780 | 4/1978 | Holley | 141/238 X |

Primary Examiner—William D. Martin, Jr.
Attorney, Agent, or Firm—Sheridan, Ross, Fields & McIntosh

[57] ABSTRACT

An apparatus is provided for filling the wells of an antibiotic plate with different concentrations of fluid including an array of fluid containers, each having a single needle valve inserted through a stopper member which is held in an open end of the container. Each needle valve includes an inner tube for supplying pressurizing air to one end of the containers which forces the fluid through an outer tube of the needle valve and out the opposite end of the container. A length of flexible tubing connected to each of the needle valve outer tubes carries the fluid through one of a plurality of slots formed in a pinch valve assembly. The pinch valve assembly includes slide members and resilient pinch rods extending laterally from sides thereof. In a first position, the slide members are held such that the pinch rods close the flexible tubing to prevent passage of the fluid into the wells of the antibiotic plate. In a second position, the slide members are held such that the pinch rods do not closably engage the tubing but permit the passage of fluid into the wells. The resiliency of the pinch rods minimizes the criticality of providing lengths of flexible tubing having the same cross-sectional size to assure proper opening and closing of the tubing.

23 Claims, 8 Drawing Figures

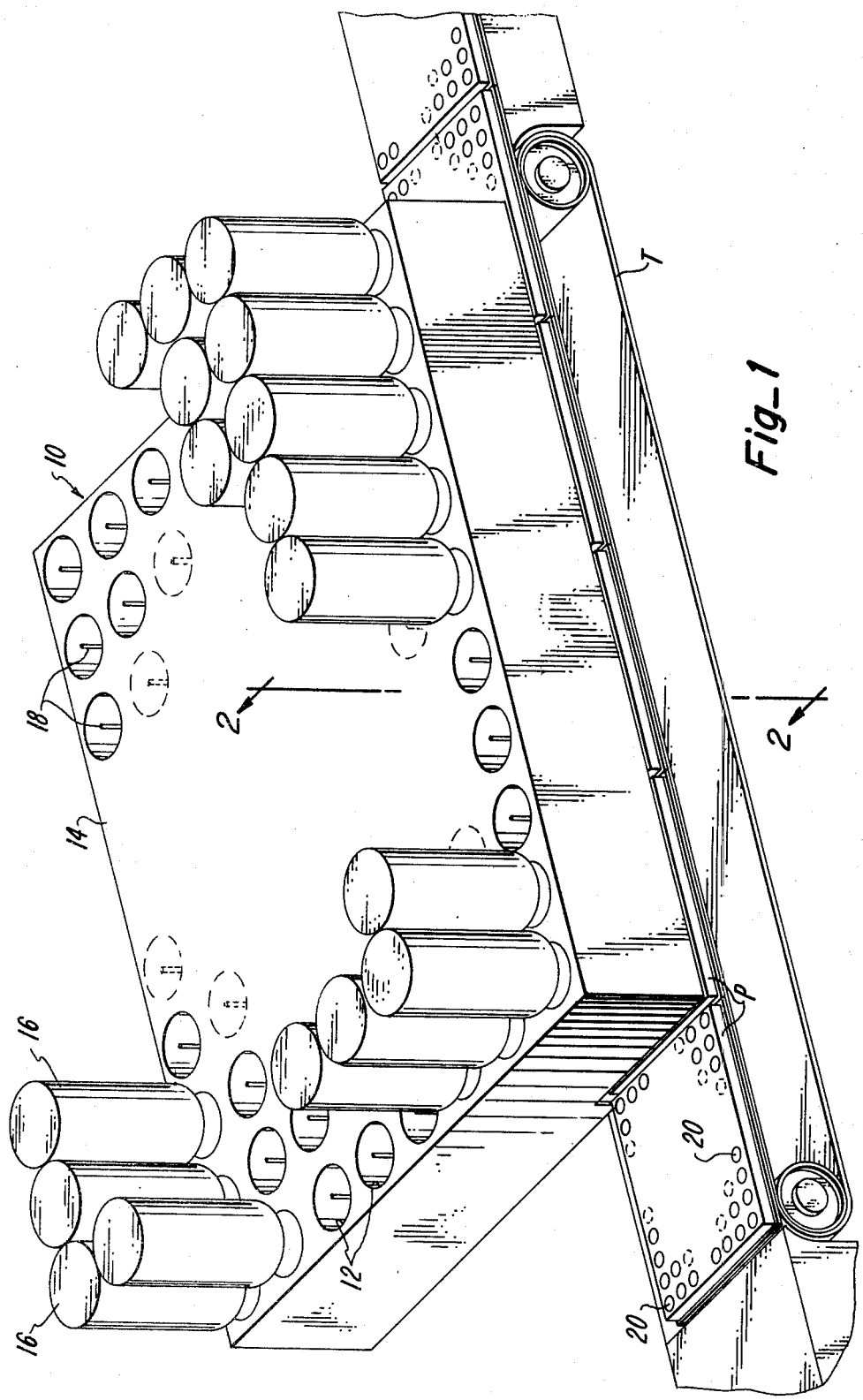

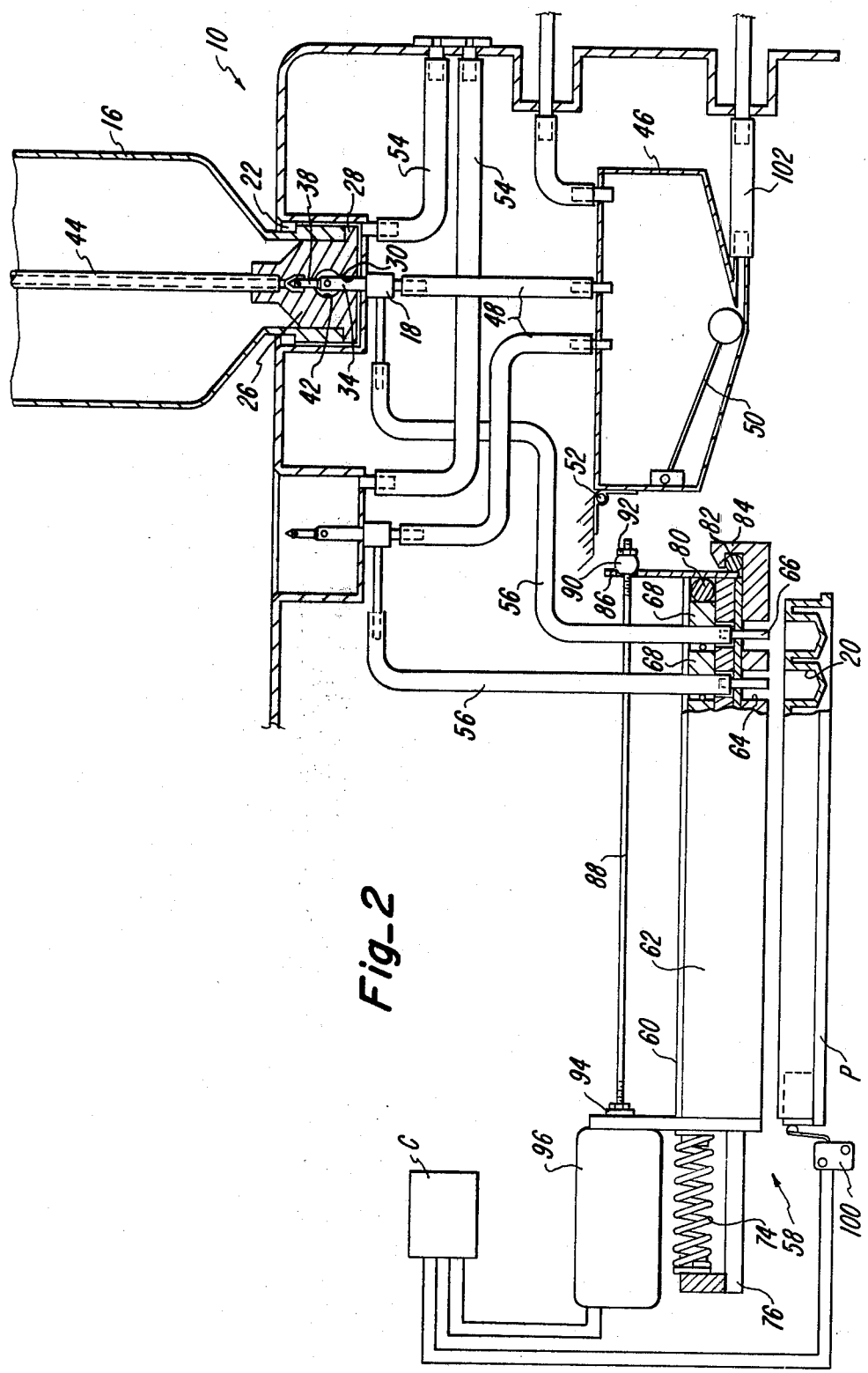
Fig_2

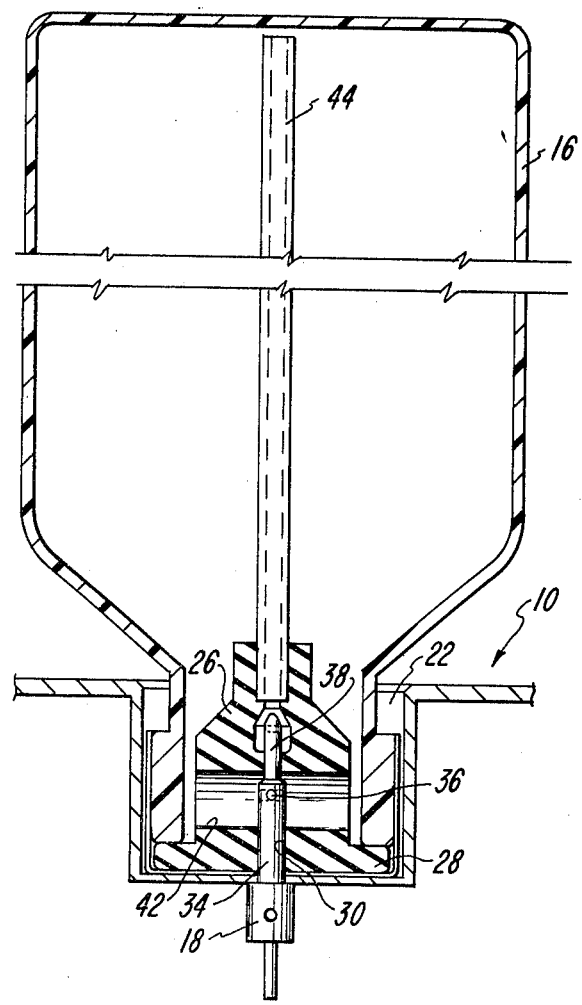
Fig_3
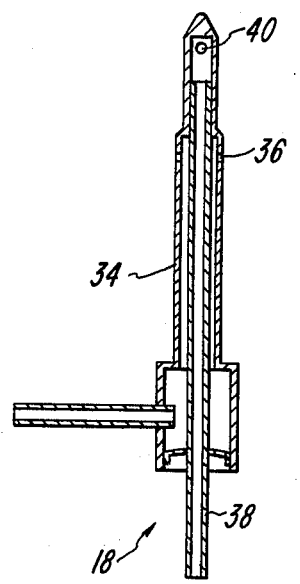
Fig_4

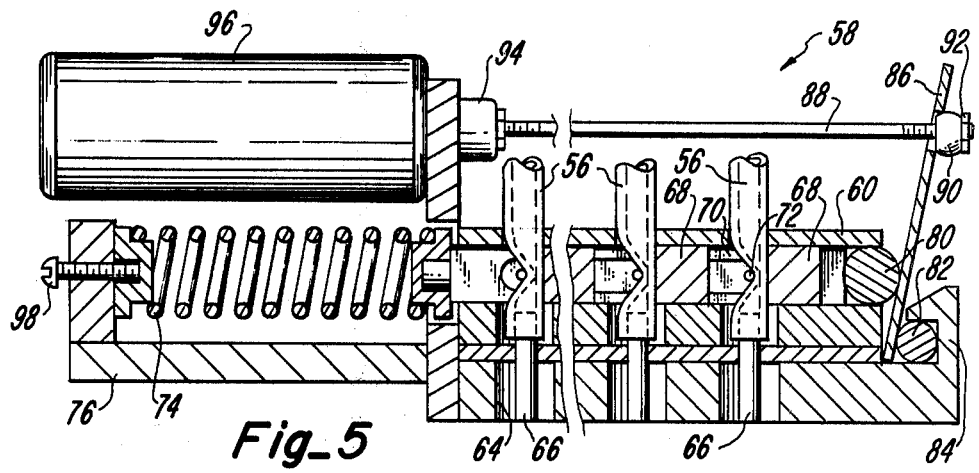
Fig_5
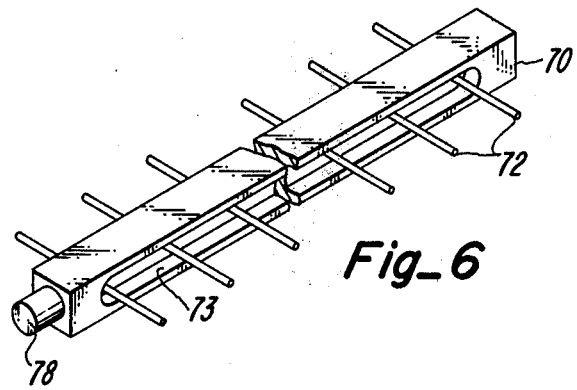
Fig_6
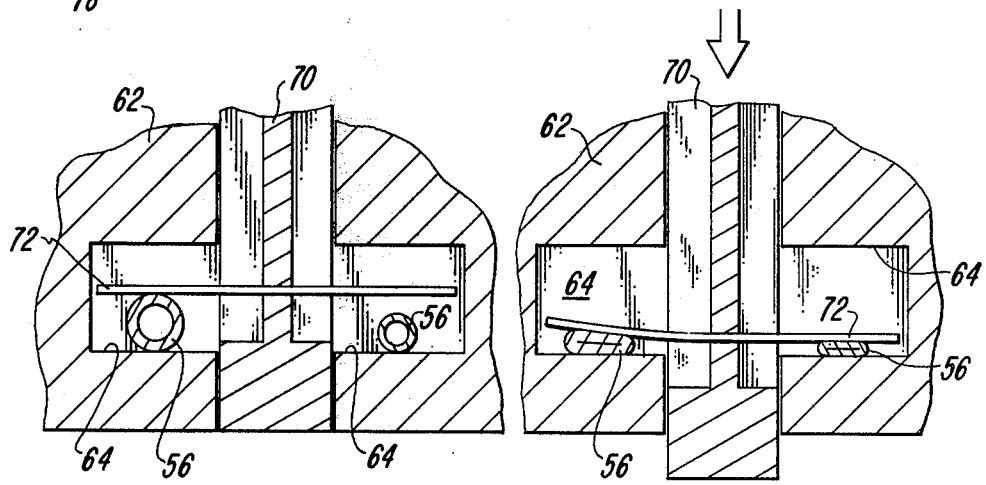
Fig_8   Fig_7

MICROPLATE FILLER

DESCRIPTION

TECHNICAL FIELD

The present invention relates to an apparatus for dispensing antibiotic solutions from a plurality of containers into wells formed in a microplate. In particular, this invention is directed to an apparatus having fluid containing bottles from which the fluid is controllably dispensed by use of needle valves and a pinch valve assembly.

BACKGROUND ART

Devices which incorporate the broad concept of controllably dispensing a fluid from a container have been developed. In U.S. Pat No. 3,014,481 to Rumble, Jr., et al. a physiological fluid injection system is shown including a flask and a pair of tubes. A first tube delivers pressurizing air to the inverted bottom of the flask to force fluid out of the flask through a second tube. In U.S. Pat. No. 3,664,549 to Maselli, Jr., a vessel containing liquid is described which can detect when predetermined liquid levels are reached in the vessel. Outflow of the liquid from the vessel, as well as inflow thereto, can be controlled. In U.S. Pat. No. 3,536,449 to Astle a serial dilution apparatus is disclosed which dilutes exact amounts of liquid to form a first dilution while simultaneously providing an exact amount of buffer solution for a succeeding dilution. In U.S. Pat. No. 4,085,780 to Holley, a liquid dispensing system is shown which uses peristaltic squeeze pumps for removing liquid from containers. In U.S. Pat. No. 4,058,146 to Citrin, a system is illustrated for transferring small amounts of liquid from a plurality of containers to a corresponding number of wells in a microtitration test plate.

DISCLOSURE OF INVENTION

In accordance with this invention, an apparatus is provided for controllably dispensing liquid held in a plurality of containers into a corresponding number of wells formed in an antibiotic plate. The apparatus includes containers for housing the liquid. A needle valve is inserted in each of the containers to provide an outlet for the liquid into a length of tubing. The tubing from each of the needle valves passes through slots in a pinch valve assembly while the discharge ends of the tubing overlie the wells of the antibiotic plate. When the pinch valve assembly is in a first or closed position, the liquid in the containers is prevented from entering the wells. When the pinch valve assembly is in a second or open position, the liquid flows from each of the containers through its attached tubing to its corresponding well.

More particularly, an antibiotic or microplate filler is provided for use in antimicrobic susceptibility testing in which a number of wells in the microplate each receive a similar amount of antibiotic solution. The solution is housed in a plurality of containers such that a different concentration of solution is housed in each of the containers. A cover assembly fixedly attaches to an opened end of each of the containers to prevent unwanted escaping of the solution. The cover assembly includes a cap member and a stopper member positioned therein. The stopper member has a channel centrally formed therein for receiving a needle valve at a first end of the stopper member and an air tube at a second end of the stopper member. The length of the air tube is such that it extends beyond the solution in the container. The needle valve includes an outer tube surrounding an inner tube, a portion of which extends beyond the outer tube. Pressurizing air is delivered through the inner tube and subsequently through the air tube to force the solution out of the container through the outer tube.

The microplate filler further includes a plurality of lengths of flexible tubing. A length of such tubing is connected to each of the needle valve outer tubes to carry the solution therefrom to its corresponding well in the microplate. The flexible tubing passes through slots in a frame of a pinch valve assembly. Each slot overlies a microplate well so that the discharge ends of the tubing are received by the wells. The pinch valve assembly further includes slide members positioned in grooves formed in the frame, a number of thin resilient pinch rods laterally extending therefrom, and a plurality of ribs formed integral with the frame. A biasing spring is operably connected at a first end of each of the slide members to urge the slide member against a first cylindrical bearing. On the opposite side of the first bearing a pivoting plate is positioned which is operably connected to a solenoid. When the solenoid is in its deenergized state, each of the springs urges its slide member in a first direction so that the pinch rods traverse the slots and contact the flexible tubing inserted therethrough. Each length of tubing is pinched between one of the pinch rods and one of the ribs so that the solution is unable to continue through the tubing into the well. When the solenoid is energized, the pivoting plate is pulled towards the first end of each slide member. This movement also forces the first cylindrical bearing to move the slide members in a second direction against the force exerted by the spring. Consequently, the pinch rods are moved away from the lengths of flexible tubing as the slide member moves, thereby permitting the flow of solution into the wells.

The microplate filler also includes an air tank positioned intermediate the needle valve inner tube and the source of air pressure. During normal operation the pressurizing air against the solution at a first end of the container forces the solution out of the container through the needle valve outer tube. Since the discharge end of the air tube extends beyond the solution, the solution is unable to enter the air tube. However, if solution should unexpectedly enter the air tube, it passes to the air tank. The air tank includes a float arm and a level detector so that a predetermined volume of solution or liquid in the air tank raises the float arm. Consequently, the level detector is activated which in turn produces a signal indicating that a predetermined volume of solution is contained in the air tank.

From the foregoing, the advantages of this invention are readily apparent. A solution container is provided having a single needle valve which passes air through its inner tube while dispensing the solution through its outer tube. The needle valve is easily inserted through the stopper member which is positioned at the open end of the container. Since the stopper member is made of a resilient material, the channel formed for insertion of the needle valve reseals upon removal thereof.

In addition, slide members supported on a frame move to either permit or inhibit the flow of solution through the flexible tubing, rather than the entire frame being moved. Thus, the solenoid-activated force required to move the slide members and the pinch rods is substantially minimized since the weight of the slide members is much less than the weight of the supporting frame. Furthermore, the pinch rods are thin and cylindrically shaped so that they do not cut into the flexible tubing when the tubing is held between the pinch rods and the ribs on the frame. This tube pinching arrangement is in contrast to the operation of a sliding frame or plate which pinches off the tubing, since in such a configuration there is a relatively greater possibility that the edges of the plate will cut the tubing after continued use. An additional significant feature of the pinch rods is that they are made of a resilient material. Thus, the pinch rods bend upon contacting the flexible tubing with sufficient force. Consequently, when the cross-sectional size of the solution-carrying tubing adjacent one pinch rod is larger than another length of tubing adjacent another pinch rod, the pinch rod contacting the larger sized tubing bends so the other rod is able to contact and close the smaller sized tubing. It can be appreciated, therefore, that strict uniformity of tubing size is not critical in the operation of closing and opening the tubing.

Also, the rolling action of the cylindrical bearings substantially reduces the friction that must be overcome when the solenoid is energized to pull the pivoting plate and in turn move the slide members and pinch rods so that the lengths of flexible tubing are open. Similarly, minimal friction is present in moving the pivoting plate when the solenoid is de-energized to close the lengths of flexible tubing. Another feature of this invention which minimizes the amount of force required to move the slide members is the difference between the connecting points of the solenoid and the slide members to the pivoting plate. The distance from the bottom portion of the pivoting plate to the solenoid connection thereto is relatively much greater than the distance from the slide members connection on the pivoting plate to the bottom portion of the pivoting plate. Since the pivoting plate acts like a lever in its pivoting movement about its bottom portion, the force of the solenoid required to move the pivoting plate when opening the lengths of tubing is substantially minimized.

A further advantage of the apparatus of this invention is the inclusion of the air tank which protects against unexpected liquid flow through an air supply conduit. Thus, solution in one container cannot enter another container through the air supply conduit and thereby contaminate the different concentrations of solutions contained therein.

Additional advantages of this invention are easily discerned from the description which follows taken in conjunction with the accompanyings drawings.

BRIEF DESCRIPTION OF THE DRAWINGS

FIG. 1 is a perspective view of the microplate filler of this invention overlying transportable microplates each having an array of wells to be filled with a liquid solution;

FIG. 2 is a vertical section, taken along lines 2—2 of FIG. 1, showing details of the microplate filler;

FIG. 3 is an enlarged view of the solution container of FIG. 2;

FIG. 4 is an enlarged, longitudinal section of the needle valve of FIG. 2;

FIG. 5 is an enlarged, fragmentary view of the pinch valve assembly of FIG. 2;

FIG. 6 is an enlarged, fragmentary, perspective view of the slide member with the pinch rods transversely extending therefrom;

FIG. 7 is a greatly enlarged, fragmentary, longitudinal section of the slide member of FIG. 5 showing the flexible tubing pinched by a pinch rod to prevent fluid flow therethrough; and FIG. 8 is a greatly enlarged, fragmentary, longitudinal section of the slide member similar to FIG. 7, but showing the flexible tubing in an opened position.

BEST MODE FOR CARRYING OUT THE INVENTION

In accordance with this invention, FIG. 1 shows a housing 10 having a number of recesses 12 formed in the top surface 14 thereof. An inverted fluid-holding container 16, such as a test tube or bottle, is placed in each of the recesses 12 so that the open end of the container 16 is adjacent the bottom portion of the recess 12. A needle valve 18 extends through an opening in each recess 12 and is connected thereto. A transporter T underlies housing 10 and carries an antibiotic plate or microplate P to a position beneath housing 10 so that wells 20 formed in the microplate P can be filled with the fluid held in containers 16. The microplate P can also be properly positioned manually beneath the housing 10, such as hand feeding by an operator, so that the wells 20 are properly aligned to receive the fluid.

Typically, containers 16 each contain an antibiotic solution having a different concentration. Such solutions are used in antibiotic susceptibility testing where substantially identical amounts of solution or liquid need to be transfered to the individual wells 20 in the microplate P. Conveniently, the number of microplate wells corresponds to the number of containers 16 so that the antibiotic solution in each container 16 can be transfered to a single well 20. The microplate wells 20 are normally formed in an array for convenient filling.

The housing 10 surrounds the means provided to transfer amounts of solution from the containers 16 to the wells 20, as best seen in FIG. 2.

A cap member 22 having a centrally formed hole covers the open end of each inverted container 16, which is conveniently threaded so that the cap member 22 is rotated and held thereon. A stopper member 26, also shown in FIG. 3, includes a circular rim portion 28 which contiguously contacts the entire inner surface of each cap member 22 to provide a seal between the cap member hole and the liquid in the container 16 and thereby prevent its escape therethrough. Each stopper member 26 has an elongated channel 30 which is formed completely through its longitudinal axis. Channel 30 is axially aligned with the hole in cap member 22 so that needle valve 18 can be inserted therethrough. As best illustrated in FIG. 4, each needle valve 18 is a single, integral unit comprising a first or outer tube 34 having a number of apertures 36 through which enters the solution held in the container 16 and a second or inner tube 38 having a number of apertures 40 through which exits a pressurizing fluid for forcing the solution out of the containers 16. Inner tube 38 is formed within outer tube 34 for a portion of its longitudinal extension while its top portion extends beyond outer tube 34. The apertures 40 are located in this top portion of inner tube 38. Since the portion of inner tube 38 within outer tube 34 has no openings and is made of a material which is impermeable to fluid, the liquid in container 16 is unable to enter inner tube 38 when needle valve 18 is properly inserted in stopper member 26. Needle valve 18 is properly inserted in channel 30 of stopper member 26 when outer tube apertures 36 are positioned in a passage 42 while inner tube apertures 40 are located beyond passage 42 in channel 30. Passage 42 is an opening laterally extending through stopper member 26 into which liquid in the container 16 flows and subsequently enters apertures 36.

Proper positioning of the needle valve apertures 36, 40 in stopper member 26 is readily achieved due to the placement of needle valve 18 in recess 12. Each needle valve 18 extends for a portion of the distance through each recess 12 such that, when stopper member 26 is inserted thereon so that it is contiguously adjacent the bottom surface of recess 12, outer tube apertures 36 are within passage 42 while inner tube apertures 40 are in channel 30 beyond passage 42.

Stopper member 26 is made of a resilient material such that a seal is formed around the outer surface of the needle valve 18 when it is twisted into the stopper member 26. Thus, liquid in container 16 cannot pass through channel 30 along the outer surface of needle valve 18. Additionally, when needle valve 18 is removed from stopper member 26, the resiliency of stopper member 26 closes or seals channel 30 so that liquid is unable to pass therethrough.

A hollow air tube 44 is placed in channel 30 adjacently above the top portion of needle valve 18. Air tube 44 extends through the liquid in the container 16 so that its discharge end is above the level of liquid. Pressurizing fluid, such as air, can then be delivered through inner tube 38 so that it exits apertures 40 into air tube 44 and is subsequently discharged at the inverted container bottom end. The pressurizing air at the inverted bottom end of the container 16 forces the liquid out through the inverted top end of the container 16 through outer tube 34.

The pressurizing air is initially supplied to a tank 46 which has a number of openings for receiving a plurality of conduit members 48. There is a conduit member 48 for each container 16 and each is connected to one inner tube 38. It can be appreciated that in normal operation liquid in container 16 cannot enter air tube 44 since its discharge end is above the liquid level. If, however, liquid should unexpectedly enter air tube 44 or any portion of inner tube 38, it flows through conduit member 48 into tank 46 and is contained therein. Tank 46 protects against liquid or solution from one container 16 unexpectedly entering another container 16 through its inner tube 38. When a predetermined level of liquid is reached in tank 46, a float arm 50 is sufficiently raised by the force of the liquid so that a signal is produced by conventional means to provide either an audible or visual indication that liquid has been detected in tank 46. Subsequent to this indication, the operation of the microplate filler can be halted while a determination is made as to the source of the malfunction. Thus, the contamination of one solution in one container with solution of a different container through conduit members 48 is virtually eliminated.

In another embodiment, a hinge member 52 supporting tank 46 can be used to initially sense that liquid is entering tank 46. A predetermined weight of liquid moves the tank 46 about the hinge member 52 which thereby provides either an audible or visual signal by conventional means indicating the detection of liquid in the tank 46.

Protection against unwanted leaks of solution through the hole in cap member 22 is provided by a drain tube 54. There is a drain tube 54 connected to an outlet formed in the bottom surface of each recess 12. If liquid should unexpectedly exit the cap member hole into recess 12, it passes to drain tube 54 which carries the liquid to a convenient storage chamber (not shown).

Each outer tube 34 is connected to a length of flexible tubing 56. Each tubing 56 has virtually the same length so that the flow characteristics of the fluid from the containers 16 is essentially the same for each length of tubing 56. The tubing 56 passes through a pinch valve assembly 58 which includes a cover plate 60 and a frame 62, as best seen in FIG. 5. The cover plate 60 has a plurality of openings, each of which receives a length of the tubing 56. An array of slots 64 is formed in frame 62 and each slot is axially aligned with a cover plate opening so that a length of flexible tubing 56 can be inserted therethrough. The discharge end of each length of tubing 56 is connected to a thin cylindrical outlet member 66, each of which overlies a well 20.

The pinch valve assembly 58 further includes a number of ribs 68 which are formed integral with frame 62 and extend vertically thereabove. The edge of each rib 68 is located contiguously adjacent and in axial alignment with one of the slots 64. A number of elongated slide members 70 are removably placed in grooves intermediate columns of ribs 68 and slots 64. Each slide member 70 has a number of thin, resilient pinch rods 72 laterally extending from the longitudinal sides thereof. The sides of the slide members 70 are formed with cavities 73 to reduce their weight and thereby lessen the amount of force required to move them during the operating of filling the microplate wells 20. The pinch rods 72 are spaced along each slide member 70 so that they travers the slots 64 which are laterally adjacent the longitudinal sides of slide member 70.

A biasing spring 74 is held by support member 76 at a first end of frame 62. A protrusion 78 formed at a first end of each slide member 70 is connected to spring 74 so that the tension of the spring 74 urges the slide member 70 in a first direction toward the opposite or second end of frame 62. The second end of each of the slide members 70 contacts a first cylindrical bearing 80 supported adjacent the second end of frame 62. A second cylindrical bearing 82 is held within a hollowed lip portion 84 of frame 62 below first bearing 80. A pivoting plate 86 is positioned between the bearings 80, 82 and is vertically supported by a threaded shaft 88 which is inserted through an opening in pivoting plate 86. A locking ball 90, having a diameter greater than the opening in pivoting plate 86, and locking nut 92 fixedly positioned pivoting plate 86 on shaft 88. The other end of shaft 88 is connected to plunger 94 of solenoid 96 which is mounted on frame 62.

It is easily understood that the distance slide member 70 is urged in the first direction by spring 74 can be adjusted by untightening locking ball 90 and locking nut 92 and moving the pivoting plate 86 along shaft 88. If locking ball 90 and locking nut 92 are positioned at the end of the shaft 88, as depicted in FIG. 5, the slide member 70 is urged to its maximum extent in the first direction. Consequently, the closing action by pinch rods 72 against flexible tubing 56 is at a maximum since the pinch rods 72 are moved more adjacent ribs 68 between which a length of flexible tubing 56 is placed. Conversely, when locking ball 90 and locking nut 92 are moved inwardly along shaft 88, pivoting plate 86 is pivoted inwardly also and forces first bearing 80 so that it pushes slide member 70 in the second direction against the force of spring 74. Consequently, pinch rods 70 can be gradually moved out of closing contact with the lengths of flexible tubing 56 by this adjustment. Since it is desirable to minimize the distance traveled by pinch rod 70 from a flexible tubing closed position to a flexible tubing open position in order to minimize the time required between opening and closing, the pivoting plate 86 is preferably moved along shaft 88 so that when solenoid 96 is not energized, all lengths of flexible tubing 56 are closed and no liquid passes therethrough. While, when solenoid 96 is energized, all lengths of flexible tubing 56 are open and the distance traveled by slide member 70 due to the pulling action of solenoid 96 is at a minimum.

The amount of tension exerted by each spring 74 against slide member 70 can be changed by adjusting bolt 98. Turning adjusting bolt 98 inwardly toward frame 62 increases the tension so that upon de-energization of solenoid 96 a relatively greater force urges slide member 70 in the first direction toward the second end of frame 62. Conversely, turning adjusting bolt 98 outwardly with respect to frame 62 decreases the spring tension.

The filling of the wells 20 of microplate P is a relatively simple yet efficient operation. Containers 16 are filled with solution and placed in recesses 12 so that needle valves 18 are twisted into stopper members 26. Pressurizing air is delivered through inner tubes 34 and forces the solution out of outer tubes 38 through lengths of flexible tubing 56 which pass through the slots 64 of pinch valve assembly 58. In a first or closed position of pinch valve assembly 58, spring 74 urges slide member 70 in a first direction such that pinch rods 72 engage the outer surface of flexible tubing 56 against an edge of ribs 68 so that the flow of solution therethrough is stopped, as illustrated in FIG. 7. When the wells 20 of microplate P are to be filled with solution, the microplate P contacts a microswitch 100, as shown in FIG. 2, which provides a signal to a controller C. By conventional means, controller C activates solenoid 96 so that plunger 94 and shaft 88 are pulled in a second direction against the tension in spring 74. Consequently, pivoting plate 86 pushes against first bearing 80 which in turn engages the second end of slide members 70 and moves the slide members 70 in the second direction. This movement of slide members 70 results in the opening of each length of flexible tubing 56 since the pinch rods 72 are moved out of closing contact therewith, as illustrated in FIG. 8. Liquid or solution can then flow into outlet member 66 and be subsequently dispensed into wells 20.

The smooth cylindrical shape of first bearing 80 and second bearing 82 minimize the friction forces that the force of solenoid 96 must overcome in moving slide members 70. When solenoid 96 is energized and pulls shaft 88 in the second direction against the force of spring 74, pivoting plate 86 moves against the round surfaces of first and second bearings 80, 82. The bottom end of pivoting plate 86 advances in the first direction against second bearing 82 which acts as a fulcrum while the portion of pivoting plate 86 adjacent first bearing 80 moves thereagainst and forces first bearing 80 to roll in the second direction. The rolling motion of first bearing 80 in frame 62 impels slide member 70 in the second direction thereby moving pinch rods 72 away from tubing 56.

When solenoid 92 is de-energized, the spring 74 forces slide member 70 in the first direction toward the second end of frame 62 causing first bearing 80 to roll against pivoting plate 86 and force it to pivot about second bearing 82. Second bearing also rolls in the second direction toward spring 74 and against pivoting plate 86 thereby preventing further movement by pivoting plate 86 in the first direction. It can be appreciated that the rolling interaction by first and second bearings 80, 82 with pivoting plate 86 and the end of slide member 70 and in frame 62 reduces friction forces and facilitates the moving of slide member 70.

Another significant feature related to the pivoting action just described is the relative locations of shaft 88 and slide member 70 with respect to pivoting plate 86. Pivoting plate 86 acts like a lever with second bearing 82 acting as the fulcrum. Since the pulling force of the solenoid 96 acts against a portion of pivoting plate 86 at a distance approximately four times farther from the fulcrum than the force of spring 74 which acts through slide member 70 against another portion of pivoting plate 86, the force required by the solenoid is substantially reduced. Consequently, a small solenoid requiring minimal energy is capable of moving the slide member 70 in the second direction to open the lengths of flexible tubing 56. Thus, both the action of the friction reducing bearings 80, 82 and the location of the solenoid activated shaft 88 on the pivoting plate 86 minimize the amount of force required to move the slide member 70.

It is also readily appreciated that a conventional timing mechanism can be housed in controller C so that, after a predetermined time interval in which a predetermined amount of solution has been dispensed into the wells 20, the solenoid 96 can be de-energized by the timing mechanism. The spring 72 then urges its attached slide member 70 back in the first direction to close off the lengths of tubing 56 and again stop the flow of liquid into the wells 20.

FIGS. 7 and 8 also illustrate a significant feature of pinch rods 72. The pinch rods 72 are thin and made of a resilient material. Because of these physical characteristics of the pinch rods 72, it is not critical that the cross-sectional size of each length of tubing 56 be the same. If one length of tubing 56 has a larger cross-sectional size than another length of tubing 56 and when the slide members 70 are in the closed position to prevent the flow of liquid to the wells 20, the end of pinch rod 72 contacting the larger sized tubing 56 bends so that the end of pinch rod 72 adjacent the smaller sized tubing is able to close that length of tubing also. The resiliency of pinch rods 72 substantially reduces the possibility that the pinch rods 72 contacting larger sized tubing 56 will prevent the closing of relatively smaller sized tubing 56. Similarly, the slide members 70 are placed in grooves formed in the frame 62 with the pinch rods 72 extending from the sides of the slide members 70 between the ribs 68. Preferably, the distance between successive ribs 68 on the frame 62 is the same as well as the spacing between the pinch rods 72 on a slide member 70 so that the distance to be traversed from a tubing opened position to a tubing closed position is the same for each pinch rod 72. Again, however, uniformity of these distances is not critical because of the resiliency of the pinch rod 72. If, for example, one pinch rod 72 on a slide member 70 has a longer distance to traverse before closing the tubing 56 than the other pinch rods 72 on the same slide member 70, the pinch rods 72 which first contact and close their lengths of tubing 56 will bend to enable the pinch rod 72 farther from its corresponding tubing 56 to contact and close its length of tubing 56 also.

Additionally, at times when the containers 16 are empty, it is often desirable to flush and thereby clean the lengths of flexible tubing 56 as well as the tubes of the needle valves 18. This capability is provided by connecting a tank tube 102 to an opening in tank 46 at its bottom portion. A flushing agent, such as water, can be delivered to the tank tube 102 and into the tank 46. Once the flushing agent reaches the top portion of tank 46, it is carried through the conduit members 48, the needle valve inner tubes 38, the air tube 44, into the containers 16 and then through the needle valve outer tubes 34, the lengths of flexible tubing 56 and finally dispensed from the outlet members 66. The tank tube 102 also provides a discharge outlet from tank 46 for any unwanted liquid that entered through conduit members 48 from inner tubes 38.

From the foregoing, the advantages of this invention are readily apparent. An apparatus is provided which controllably and efficiently dispenses liquid from a plurality of containers into corresponding wells formed in a microplate. A single, integral needle valve is easily twisted into a channel formed in a stopper member which is held in an open end of each container. When the valve is removed from the stopper member, the resiliency thereof reseals the channel so that liquid cannot flow therethrough. The needle valve unit has an outer tube for releasing the liquid held in the container while an inner tube is formed within the outer tube and extends therebeyond for supplying a pressurizing fluid to the container. Although the needle valve is an integral unit, the inner tube and outer tube have independent passageways so that the container liquid is unable to enter he inner tube through the outer tube when the needle valve is properly positioned in the stopper member.

Significantly, the pinch rods of the pinch valve assembly are thin and cylindrically shaped to minimize the possibility that the liquid-carrying flexible tubing will be cut by the contacting thereof by the pinch rods when the tubing is closed during the process of filling various microplates. Additionally, since the slide members move, rather than the entire slotted frame, to either close or open the tubing, less force is required for this sliding movement. Moreover, the pinch rods are made of a resilient material so that they are capable of bending upon contacting the lengths of tubing. Consequently, the size of the tubing is not critical nor is the spacing between the ribs on the frame and the spacing between the pinch rods in each slide member.

Another important advantage of this invention is the operation of the friction reducing bearings which facilitates the sliding movement of the slide members. This feature, as well as the positioning of the solenoid-pulled shaft on the pivoting plate, further minimize the amount of force required to move the slide members. Accordingly, a relatively small solenoid requiring substantially less energy for activation thereof is needed to move the slide members to open the lengths of tubing.

Protection agaist contamination of liquid or solution in one container by solution in another container is also provided. A tank is connected to conduit carrying the pressurizing fluid and is positioned intermediate the source of such fluid and the containers. If unwanted liquid should enter the conduit, it passes to the tank rather than to a container having a known concentration of solution. Furthermore, the tank has an opening for receiving a flushing agent which can be carried through the conduit and lengths of flexible tubing to flush the solution-containing portions of the microplate filler.

Finally, the apparatus of this invention is modular formed and sturdily constructed of stainless steel and silicone rubber so that any aqueous solution compatible therewith can be used with this microplate filler. The apparatus is also compact and can be sterilized by a standard autoclave without disassembly.

The invention has been described in detail with particular reference to preferred embodiments thereof, but it will be understood that variations and modifications can be effected within the spirit and scope of the invention.

I claim:

1. An apparatus for dispensing liquid into wells formed in a microplate, comprising:
   container means for holding the liquid which is to be dispensed into the microplate wells;
   a needle valve connected to said container means and including a first tube and a second tube formed together in an integral unit, said first tube to remove the liquid from said container means and said second tube to deliver a pressurizing fluid into said container means so that the removal of liquid therefrom is facilitated;
   said first tube surrounds a portion of said second tube while a top portion of said second tube extends outwardly of said first tube so that independent passageways are provided through said first and second tubes such that the liquid is unable to enter said second tube while the pressurizing fluid is unable to enter said first tube under normal operating conditions;
   tubing means connected to said first tube for transferring the liquid in said container means to the wells in the microplate;
   pinch valve means operably connected to said tubing means for releasably stopping the flow of liquid therethrough into the microplate wells; and
   a stopper member held in an open end of said container means and having a channel extending longitudinally therethrough and a passage extending laterally therethrough, said needle valve being inserted into said channel such that said first tube receives liquid entering said passage while said second tube delivers the pressurizing fluid into said channel portion extending beyond said passage.

2. The apparatus, as claimed in claim 1, wherein:
   said stopper member is made of a resilient material so that said channel is sealed when said needle valve is removed therefrom and liquid in said container means is unable to escape through said resealed channel.

3. The apparatus, as claimed in claim 1, further including:
   an air tube extending longitudinally through said container means and having an end adjacent said second tube for receiving the pressurizing fluid and another end above the liquid in the container means to discharge the pressurizing fluid which forces the liquid into said passage.

4. The apparatus, as claimed in claim 1, wherein said pinch valve means includes:
   a frame having a groove formed therein and a plurality of slots formed through said frame adjacent the sides of said groove for receiving said tubing means;
   a plurality of ribs extending vertically from said frame and integral therewith, one of said ribs being positioned adjacent each of said slots;

a slide member placed in said groove and movable to a first position to close said tubing means and thereby stop the liquid flow therethrough and movable to a second position to open said tubing means and thereby allow liquid to flow therethrough;

a pinch rod held in said slide member and extending laterally from the side of said slide member for closably contacting said tubing means between one of said ribs and an end portion of said pinch rod when said slide member is moved to the first position; and driving means for moving said slide member between said first and second positions.

5. The apparatus, as claimed in claim 4, wherein said driving means includes:

first means connected to a first end of said slide member to urge said slide member into the first position to prevent the liquid from flowing through said tubing means; and second means connected to a second end of said slide member to urge said slide member into the second position to enable the liquid to flow through said tubing means.

6. The apparatus, as claimed in claim 5, wherein: said first means includes a biasing spring.

7. The apparatus, as claimed in claim 5, wherein said second means includes:

a solenoid mounted on said frame and having an extendable plunger;

a shaft connected to said plunger at a first end;

a pivoting plate pivotably supported in said frame and having an opening adjacent the top portion thereof;

locking means for securing a second end of said shaft to said pivoting plate through its opening;

a first cylindrical bearing supported by said frame intermediate said pivoting plate and said second end of said slide member so that upon energization of said solenoid, said plunger pulls said shaft and said pivoting plate, said pivoting plate in turn advances against said first bearing and said first bearing subsequently rolls in said frame to impel said second end of said slide member to the second position thereby opening said tubing means and permitting the liquid to flow therethrough into the microplate wells.

8. The apparatus, as claimed in claim 7, wherein said second means further includes:

a second cylindrical bearing supported in said frame adjacent the side of said pivoting plate at a bottom portion thereof opposite said first bearing, said second bearing acting as a fulcrum about which said pivoting plate pivots when said solenoid is energized.

9. The apparatus, as claimed in claim 8, wherein:

the distance between said shaft connection on said pivoting plate and said fulcrum-acting second bearing is relatively greater than the distance between said slide member second end connection on said pivoting plate and said fulcrum-acting second bearing so that the force required to move said pivoting plate while opening said tubing means is substantially less than the force required to move said pivoting plate while closing said tubing means.

10. The apparatus, as claimed in claim 4, wherein: said pinch rod has a rounded surface for contacting said tubing means so that, when said pinch rod closes said tubing means, the cutting thereof by said pinch rod is minimized.

11. The apparatus, as claimed in claim 4, wherein:

said pinch rod is thin and made of a resilient material so that upon forcably contacting said tubing means said pinch rod is bendable to minimize the need for strict cross-sectional uniformity among lengths of said tubing means.

12. An apparatus for dispensing liquid into wells formed in a microplate, comprising:

a plurality of containers, each of said containers holding liquid which is to be dispensed into the microplate wells;

valve means connected to each of said containers, said valve means including a first tube for removing the liquid from said container and a second tube, independent of said first tube, for delivering a pressurizing fluid into said container to facilitate the removal of liquid therefrom;

tubing means connected to said first tube of said valve means for transfering the liquid in said container to a well in the microplate;

conduit means connected to said second tube of said valve means for carrying the pressurizing fluid to said container;

tank means connected to said conduit means for containing unwanted liquid that unexpectedly enters said conduit means to prevent the liquid from one of said containers entering another of said containers through said second tube of said valve means; and pinch valve means operably connected to said tubing means for releasably stopping the flow of liquid therethrough into the microplate wells.

13. An apparatus for dispensing liquid under pressure, comprising:

a container for holding the liquid;

a stopper member held in an open end of said container to seal said container open end, said stopper member including a channel extending longitudinally theethrough and a passage intermediate portions of said channel extending laterally through said stopper member;

a needle valve inserted in said stopper member, said needle valve including a first tube and a second tube formed together in an integral unit, said first tube for removing liquid in the container and said second tube, being independent of said first tube so that liquid is unable to enter under normal operating conditions, for delivering a pressurizing fluid to said container and thereby facilitating the removal of the liquid;

said first tube surrounds a portion of said second tube and including an aperture positioned in said passage to receive the liquid entering said passage from said container; and said second tube including a top portion which extends outwardly beyond said first tube in said channel, said top portion of said second tube having an aperture to deliver the pressurizing fluid to said container.

14. The apparatus, as claimed in claim 13, further including:

a threaded cap member releasably holding said stopper member in said container open end and having an opening to permit entry of said needle valve into said stopper member.

15. The apparatus, as claimed in claim 14, wherein:

said stopper member includes a rim contiguous with said cap member opening to prevent liquid from escaping said container through said cap member opening.

16. The apparatus, as claimed in claim 13, wherein: said stopper member is made of a sealable, resilient material such that liquid is unable to pass through said channel upon removal of said needle valve therefrom.

17. An apparatus for releasably preventing the flow of liquid through lengths of tubing comprising:
a frame having a groove and a number of slots adjacent the sides of said groove to receive the lengths of tubing;
a plurality of ribs supported by said frame, one of said ribs being positioned adjacent each of said slots;
a slide member having a first end and a second end and placed in said groove;
a pinch rod connected to said slide member and extending laterally therefrom and adjacently across one of said slots;
driving means connected to said first end of said slide member for moving said slide member in a first direction so that said pinch rod engages and closes one length of tubing and prevents liquid flow therethrough; and
impelling means connected to said second end of said slide member for moving said slide member in a second direction so that said pinch rod moves away from and thereby opens the length of tubing.

18. The apparatus, as claimed in claim 17, wherein said impelling means includes:
a first cylindrical bearing supported on said frame adjacent said second end of said slide member;
a pivoting plate pivotably supported in said frame and having a portion thereof contiguous with said first bearing;
a shaft connected to said pivoting plate at a first end;
pulling means connected to a second end of said shaft for enabling said pivoting plate to pivot in the second direction so that said pivoting plate moves said first bearing which in turn rollably forces said second end of said slide member in the second direction.

19. The apparatus, as claimed in claim 18, wherein: said pulling means includes a solenoid having an extendable plunger connected to said second end of said shaft.

20. The apparatus, as claimed in claim 18, further including:
a second cylindrical bearing supported in said frame adjacent the bottom portion of said pivoting plate at a surface thereof opposite the surface contacting said first bearing, said second bearing acting as a fulcrum about which said pivoting plate pivots and facilitating the movement of said pivoting plate during the opening and closing of the length of tubing.

21. The apparatus, as claimed in claim 20, wherein: the distance between said shaft connection on said pivoting plate and said fulcrum-acting second bearing is relatively greater than the distance between said slide member second end connection on said pivoting plate and said fulcrum-acting second bearing so that the force required to move said pivoting plate while opening said tubing means is substantially less than the force required to move said pivoting plate while closing said tubing means.

22. The apparatus, as claimed in claim 17, wherein: said pinch rod has a rounded surface for contacting the length of tubing so that, when said pinch rod closes the length of tubing, the cutting thereof by said pinch rod is minimized.

23. The apparatus, as claimed in claim 17, wherein: a plurality of spaced pinch rods are connected to said slide member, each of said pinch rods extends across one of said slots adjacent a length of tubing, said pinch rods being bendable so that one of said pinch rods is movable for a greater distance than another of said pinch rods when closing a length of tubing to minimize the need for strict cross-sectional uniformity among the lengths of tubing and also minimize the need for strict uniformity with regard to the spacing between said pinch rods in said slide member.

* * * * *